United States Patent
Mushahwar et al.

(10) Patent No.: US 9,381,340 B2
(45) Date of Patent: Jul. 5, 2016

(54) APPARATUS AND METHOD FOR ELECTRICALLY STIMULATING PRESSURE-LOADED MUSCLES

(71) Applicant: Prev Biotech Inc., Edmonton (CA)

(72) Inventors: Vivian Mushahwar, Edmonton (CA); Glen Isaacson, Edmonton (CA); Alisa Ahmetovic, Edmonton (CA); Ryan Sommer, Edmonton (CA)

(73) Assignee: PREV BIOTECH INC., Edmondton (CA)

( * ) Notice: Subject to any disclaimer, the term of this patent is extended or adjusted under 35 U.S.C. 154(b) by 0 days.

(21) Appl. No.: 14/369,554

(22) PCT Filed: Jan. 31, 2013

(86) PCT No.: PCT/CA2013/000087
§ 371 (c)(1),
(2) Date: Jun. 27, 2014

(87) PCT Pub. No.: WO2013/113099
PCT Pub. Date: Aug. 8, 2013

(65) Prior Publication Data
US 2015/0057734 A1    Feb. 26, 2015

Related U.S. Application Data

(60) Provisional application No. 61/593,175, filed on Jan. 31, 2012.

(51) Int. Cl.
| | |
|---|---|
| A61N 1/00 | (2006.01) |
| A61N 1/04 | (2006.01) |
| A61F 13/06 | (2006.01) |
| A61N 1/36 | (2006.01) |
| A61G 7/057 | (2006.01) |

(52) U.S. Cl.
CPC ............ *A61N 1/0484* (2013.01); *A61F 13/069* (2013.01); *A61N 1/0452* (2013.01); *A61N 1/0492* (2013.01); *A61N 1/36003* (2013.01); *A61G 7/057* (2013.01); *A61G 2203/34* (2013.01)

(58) Field of Classification Search
CPC ... A61N 1/0452; A61N 1/0484; A61G 7/057; A61G 2203/34
See application file for complete search history.

(56) References Cited

U.S. PATENT DOCUMENTS

| | | | |
|---|---|---|---|
| 4,117,846 A | 10/1978 | Williams | |
| 4,727,878 A | 3/1988 | Levine | |
| 2006/0111652 A1 | 5/2006 | McLeod | |
| 2011/0263950 A1* | 10/2011 | Larson et al. | 600/301 |
| 2012/0302821 A1* | 11/2012 | Burnett | 600/14 |
| 2014/0207050 A1* | 7/2014 | Gonzalez et al. | 604/21 |
| 2015/0032184 A1* | 1/2015 | Muccio | 607/48 |
| 2015/0165222 A1* | 6/2015 | Oskin et al. | 600/388 |

FOREIGN PATENT DOCUMENTS

| | | |
|---|---|---|
| EP | 2165733 A1 | 3/2010 |
| WO | 9312834 A1 | 7/1993 |

* cited by examiner

*Primary Examiner* — Robert N Wieland
(74) *Attorney, Agent, or Firm* — Marsh Fischmann & Breyfogle LLP; Jonathon A. Szumny

(57) ABSTRACT

An apparatus and method of using same for preventing pressure ulcers is provided. More specifically, the present apparatus and method may be used in individuals having compromised mobility and/or lack of sensation to prevent pressure ulcers by electrically stimulating pressure-loaded or compressed muscles.

18 Claims, 9 Drawing Sheets

APPARATUS AND METHOD FOR ELECTRICALLY STIMULATING PRESSURE-LOADED MUSCLES

TECHNICAL FIELD

The present disclosure relates to an apparatus and method of using same for preventing pressure ulcers. More specifically, the present apparatus and method may be used in individuals having compromised mobility and/or lack of sensation to electrically stimulate pressure-loaded or compressed muscles.

BACKGROUND

Pressure ulcers (also known as "bed sores" or "pressure sores") are typically associated with individuals having compromised mobility or lack of sensation, such as the infirm, elderly and people suffering from stroke, spinal cord injury, bone and joint disease, vascular pathologies, tumours and diabetes. People in intensive care units, hospital wards, or undergoing long surgical procedures are also at risk of developing pressure ulcers.

A pressure ulcer is a tissue abnormality or lesion resulting from pressure imposed upon soft tissue underlying skin, fat, fascia, muscle, bone, or any combination thereof. Following prolonged periods of loading (e.g., compression, tension and shear), the soft tissue positioned between a bony prominence (e.g. the ischial tuberosities, trochanter, shoulder blades, sacrum) and an external surface (e.g. bed, wheelchair) begins to deform and break down. Soft tissue breakdown results from the sustained deformation of tissue and the occlusion of capillaries and ischemic reduction of blood flow (i.e. a reduction of oxygen, nutrients, and removal of metabolic waste products) to the loaded tissue region.

Current techniques employed to prevent pressure ulcer formation include frequent repositioning of the individual, and the use of specialized cushions and mattresses that provide some pressure relief of the tissues at risk. However, effective administration of these pressure-relieving techniques is difficult, expensive and often dependent upon patient compliance. Repositioning of patients must achieve pressure relief to the tissue and must be performed either by hospital staff, caregivers or by encouraging the patient to perform wheelchair push-ups or side-to-side leans. For wheelchair push-ups, the patient has to sustain a push up for at least 1 minute and 53 seconds for the intervention to be effective. This often cannot be done because the patients do not have the arm mobility or strength to perform his maneuver. Specialized wheelchair cushions are commonly used but specialized mattresses are heavy, expensive and not widely utilized. Further, these techniques merely provide passive tissue load reduction, thereby failing to actively engage the patient's own muscles.

Electrical stimulation of muscle tissue, commonly known as electrical muscle stimulation (EMS), has been examined as a means for preventing or mitigating pressure ulcer formation. EMS applied to loaded muscles produces active contraction thereof, dynamically deforms and reshapes the loaded muscle. Reshaping of the mechanically compressed and ischemic muscle reduces tissue injury by redistributing pressure, relieving tissue deformation, restoring blood flow and increasing oxygenation of the target tissue, particularly where the stimulation of the muscle is applied to mimic the natural postural shifts or "fidgeting" of able-bodied individuals.

Currently, in order to achieve accurate and effective electrode placement, EMS electrodes must either be implanted or applied directly on the skin of the patient. However, implanted or direct contact of electrodes with the skin can cause problems. For instance, direct contact can result in irritation of the wearer's skin due to the lack of electrode breathability, the chemical adhesives used, or weakening of the skin with repeated use. Electrode directly applied to the skin can also peel off, rolling up at the edges or bunch up. Where treatment is ongoing, superficial skin injury can occur from continual "ripping off" of the electrodes and hair removal may often be required.

Garments can be configured to administer electrical stimulation without direct electrode-skin interface. For example, garments may have electric coils integrated therein, while others have electrodes removably positioned at pre-determined locations within the garment using snaps or velcro. However, "fixed-placement" garments are limited and electrode positioning is unchangeable from patient to patient.

Some garments, such as that described in United States Patent Application No. US2010/0185259 A1, provide "openings" in the garment (e.g. mesh or netting portions between the electrodes and the person's skin) for securing electrodes, while providing flexibility in electrode positioning. These garments, however, are designed for rehabilitative or exercise purposes (e.g. to contract biceps and quadriceps), that is—to train muscles by taking advantage of the fact that electrical stimulation can be applied to build muscle mass and strength. As such, it is desirable that the openings are operative to provide breathability and to reduce electrode displacement caused when the user becomes sweaty during the workout session.

There is a need for an apparatus and method for use in preventing pressure ulcers in individuals having compromised mobility and/or lack of sensation. Such an apparatus and method may be capable of electrically stimulating pressure-loaded or compressed muscles over long periods of time, without requiring that the electrodes directly adhere to the skin and without causing further mechanical pressure points.

SUMMARY

The present apparatus and method of using same were developed in connection with a process for preventing pressure ulcers, such as the "intermittent electrical stimulation" (IES) process defined in U.S. patent application Ser. No. 13/550,371. A research effort was initiated to develop an apparatus and method appropriate for long-term use in individuals having compromised mobility and/or sensation. It was gradually discovered, through hundreds of trial and error experiments, that such an apparatus and method should be capable of alleviating pressure and increasing oxygenation of loaded muscles, without requiring (or minimizing the requirement) that the electrodes directly adhere the skin of the wearer and without causing further mechanical stress points.

The present apparatus and method of using same may be for use in stimulating loaded muscles of the human body, to effect contraction thereof, even intermittently, without requiring that the electrodes be implanted or directly adhered to the skin (e.g. externally applied, low adhesion, reduced-adhesion electrodes). Such an apparatus may be comfortably worn by an individual with compromised mobility for long periods of time, and may be easily removed and replaced. Such an apparatus may be reliably and consistently utilized by the wearer without the assistance of a caregiver.

The present apparatus and method of using may be capable of stimulating loaded muscles of the human body to reconfigure the shape of the muscle, thereby temporarily redistributing pressure away from the loaded muscle. Such stimulation may be implemented to mimic natural muscle deformation and reshaping that occurs in able-bodied individuals during postural weight shifting or "fidgeting".

The present apparatus and method of using same may be capable of providing effective, consistent and reliable delivery of electrical stimulation for long periods of time (e.g. many hours per day on a daily, weekly or monthly basis), without rolling, curling or bunching of electrodes. The present apparatus and method of using same may provide means for the wearer to remove and replace the electrodes for stimulation without harming their skin and with minimal discomfort.

These aims are satisfied by constructing a composite (e.g. three layer) apparatus such as, for example, a garment fabricated from a first layer of flexible (stretchy), yet taut, form-fitting material having a second layer of material having "openings" disposed therein, at or near the location of a loaded muscle on the wearer's body. The openings may comprise non-stretchy, non-conductive mesh material capable of receiving and securing electrodes. The "openings" may be configured such that the mesh material, which may be positioned between the electrodes and the wearer's skin, does not move relative to the skin (i.e. the mesh material moves and behaves similar to the skin of the wearer to prevent tugging on the skin). The garment may further comprise a third layer of loose-fitting material, for providing a "back panel" portion covering the openings and capable of preventing movement or displacement of the electrodes caused when the garment is in use (e.g. "snagging" of electrodes when the wearer rubs against the wheelchair or bed). The back panel may further provide visibility of the electrodes and their position on the wearer, which can be difficult when the wearer is in a supine or recumbent position.

Generally and without limitation, one embodiment of the present apparatus may comprise a composite garment consisting of at least:

a) a form-fitting, stretchy main body portion that is easy to put on and take off, and that comfortably maintains its shape on the wearer;

b) at least one non-stretchy opening portion, disposed within the main body portion at or near the location of a motor point of a loaded muscle(s), for receiving and securing at least one electrode, that is configured to move in conjunction or in association with the skin; and c) a loose-fitting back panel portion, for covering the at least one opening portion, and preventing pulling or tugging on the electrodes and garment caused by friction from the external environment (e.g. a wheelchair or bed), without causing the wearer of the garment slip.

The aims are further satisfied by constructing the present composite garment such that, when worn, the garment rests as flush as possible with the skin of the wearer without causing further mechanical stress points or pressure injuries. For example, fabrication of the garment, the material and electrodes used, and the connecting terminals may all be designed to be smooth and flush with the skin of the wearer so as to minimize mechanical stress points.

These aims are further satisfied by constructing a composite apparatus such as, for example, a shirt or undershirt-like garment for stimulating loaded muscles on the wearer's upper body or torso.

These aims are further satisfied by constructing a composite apparatus such as, for example, a sheet or mattress pad cover for stimulating the loaded muscles of an individual laying in a bed.

The present apparatus and method may also be beneficial for, without limitation, alleviating pain or discomfort from prolonged loading of muscles such as, for example, when an individual remains sitting for long periods of time (e.g. helpline operators, long-distance drivers/pilots, long-distance travelers).

Broadly, an apparatus is provided for preventing pressure ulcers in a loaded muscle, the apparatus comprising a stretchy, form-fitting main body portion, at least one non-stretchy, opening portion positioned within the main body portion at or near the loaded muscles, at least one electrode, removably received and secured by the opening portion, for stimulating the loaded muscles and to effect contraction thereof, thereby redistributing pressure of, and increasing oxygenation in, the loaded muscles. The apparatus may comprise a garment that can be worn to cover the upper body, the lower body or both. The apparatus may further comprise a sheet or mattress pad cover.

A method of stimulating loaded muscles in a person having compromised mobility is further provided, the method comprising the steps of: a) providing an apparatus capable of stimulating at least a portion of the loaded muscle, wherein the apparatus comprises: a stretchy, form-fitting main body portion, at least one non-stretchy, opening portion disposed within the main body portion at or near the loaded muscle, at least one electrode, removably received and secured by the opening portion for stimulating the loaded muscles, and b) stimulating the loaded muscles, through the at least one opening portion, to effect contraction of the loaded muscles, wherein contraction redistributes pressure and increases oxygenation in the loaded muscle.

DESCRIPTION OF THE DRAWINGS

The present apparatus and method will be better understood when consideration is given to the following detailed description thereof. Such description makes reference to the annexed drawings wherein.

DESCRIPTION OF THE EMBODIMENTS

The present apparatus and method relate to garment-like embodiments 10, 20 and/or to mattress pad-like embodiment 30 for preventing pressure ulcers, and will be described having regard to FIGS. 1-9. Without limitation, some embodiments are described with greater specificity than others to omit redundant explanation of common basic structure.

FIGS. 1-5 depict a first exemplary pant-, short- or underwear-like garment embodiment 10 of the present apparatus. Garment 10 may be fabricated to cover the lower torso and legs of the human body, and configured to provide electrical stimulation to regions of the human body that experience pressure (e.g. near sitting bones) such as, for example, the muscle and skin surrounding the ischial tuberosities, the sacrum, and the trochanter. The garment 10 may be configured of at least two layers or types of material such as, for example, a stretchy, form-fitting layer that is capable of moving in parallel with the wearer, for maintaining electrode connection with the wearer, and a loose-fitting layer that is capable of moving independently of the form-fitting layer and the wearer, for preventing tugging, curling or rolling of electrodes caused when the wearer rubs against the external environment (e.g. a chair or bed). The first form-fitting layer may further comprise at least one opening portion disposed therein, for reducing electrode adhesion (but not electrical conductivity) with the skin of the wearer.

Figure 6:
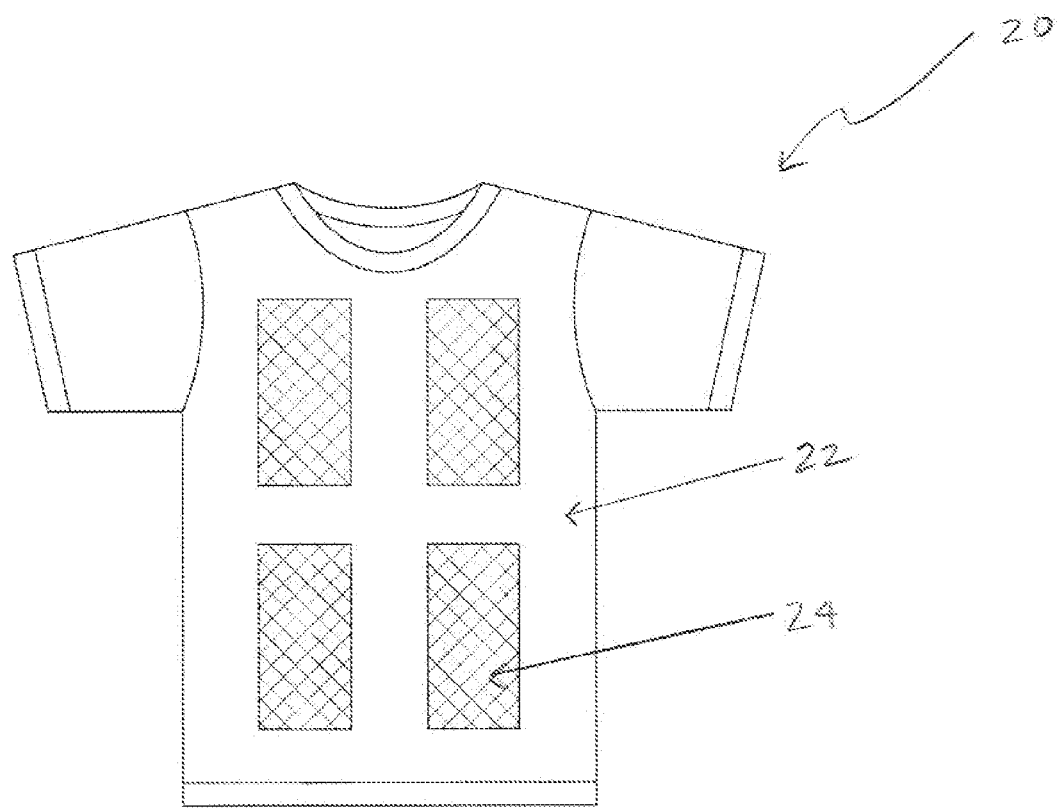
FIG. 6 shows a rear view of a second exemplary shirt-like garment embodiment for electrically stimulating a loaded muscle(s)
Figure 7:
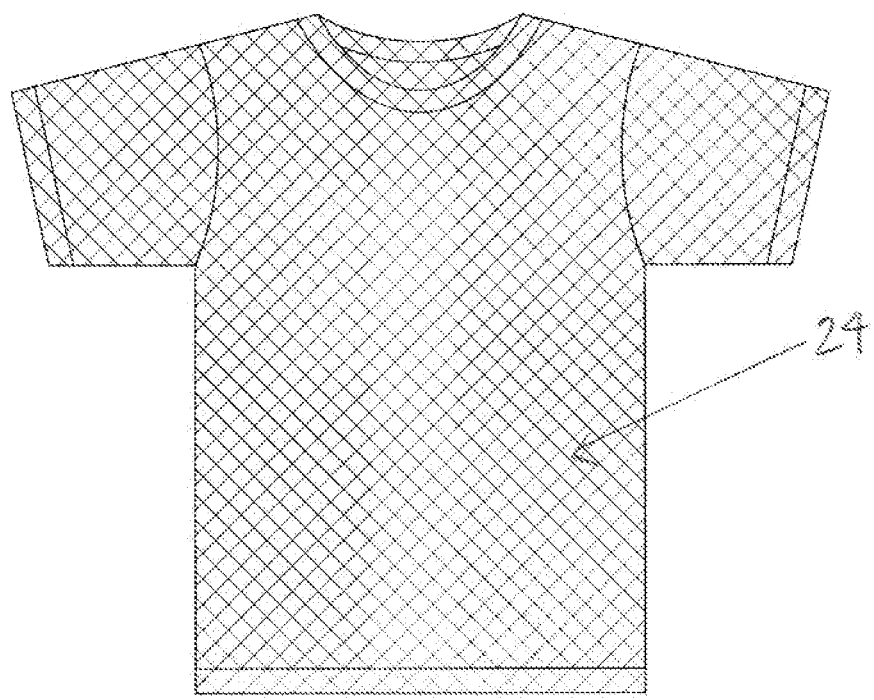
FIG. 7 shows a rear view of a second exemplary shirt-like garment embodiment for electrically stimulating a loaded muscle(s)

FIGS. 6-7 depict a rear view of a second exemplary shirt- or undershirt-like garment embodiment 20 of the present apparatus. Garment 20 may be fabricated to cover the upper torso and back of the human body, and configured to electrically stimulate regions of the body that experience pressure (e.g. near the shoulder blades). Garment 20 may further be capable of electrically stimulating the muscle and skin to, for example, assist with retaining an upright posture while sitting in a wheelchair, to assist in sitting up straight after leaning forward in people with reduced control of back muscles, to assist with coughing in people with high spinal cord injury, to exercise key trunk, shoulder, abdomen and chest muscles, or to increase muscle mass.

Figure 8:
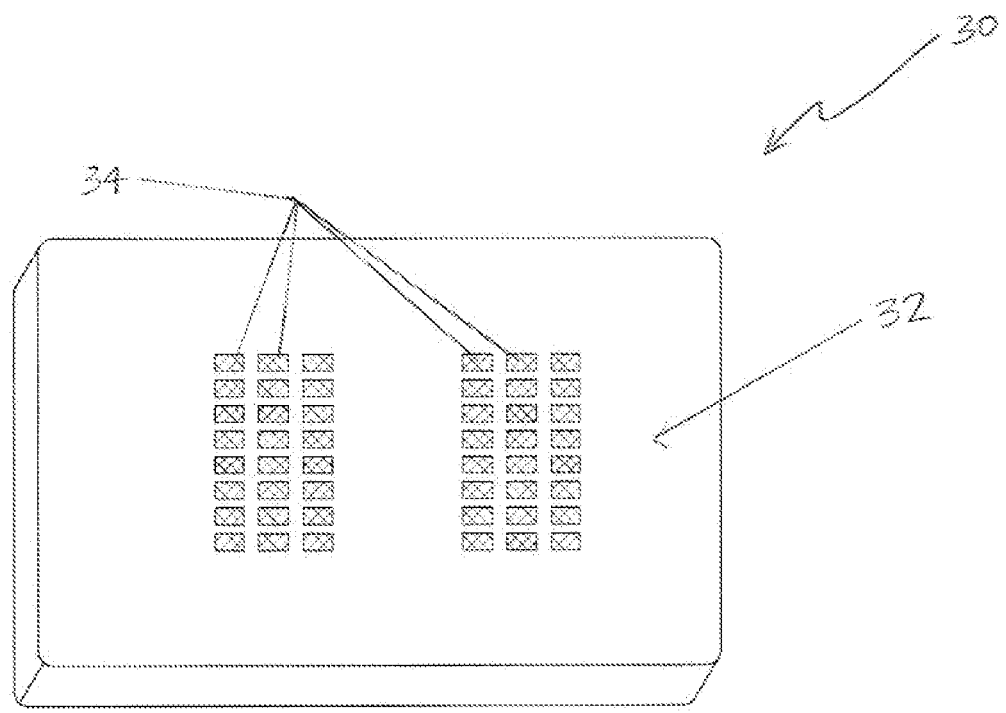
FIG. 8 shows a third exemplary sheet or mattress-pad cover embodiment.
Figure 9:
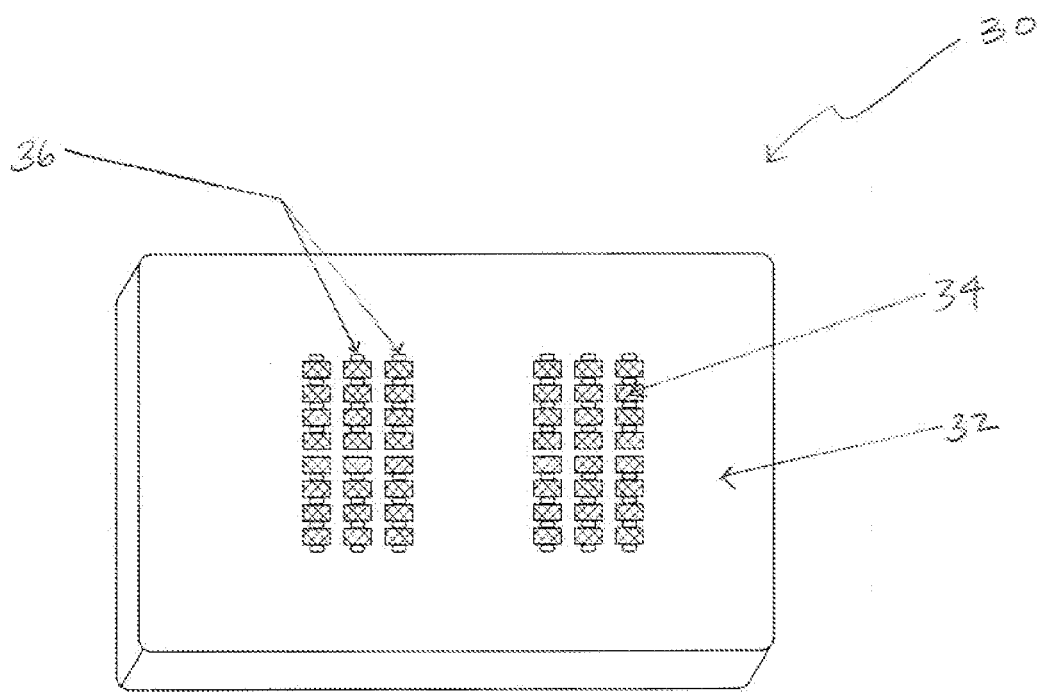
FIG. 9 shows the third exemplary sheet or mattress-pad cover embodiment comprising pressure sensors.

FIGS. 8-9 depict a third exemplary mattress pad cover or sheet-like embodiment 30 of the present apparatus. Mattress-pad 30 may be configured to apply electrical stimulation to the muscle and skin of a person at risk of developing pressure ulcers in bed-bound individuals (e.g. shoulder blades, sacrum, trochanters). Mattress pad 30 may further be capable of alleviating chronic pains, for exercise and for increasing muscle mass.

More specifically, and without limitation, garment 10 may be a composite garment (e.g. at least two varieties of fabric). For example, garment 10 may comprise a first stretchable main body portion 12 and at least one non-stretchable "opening" portion 14. Garment 10 may further comprise a third stretchable and loose fitting back panel portion 16.

Figure 1:
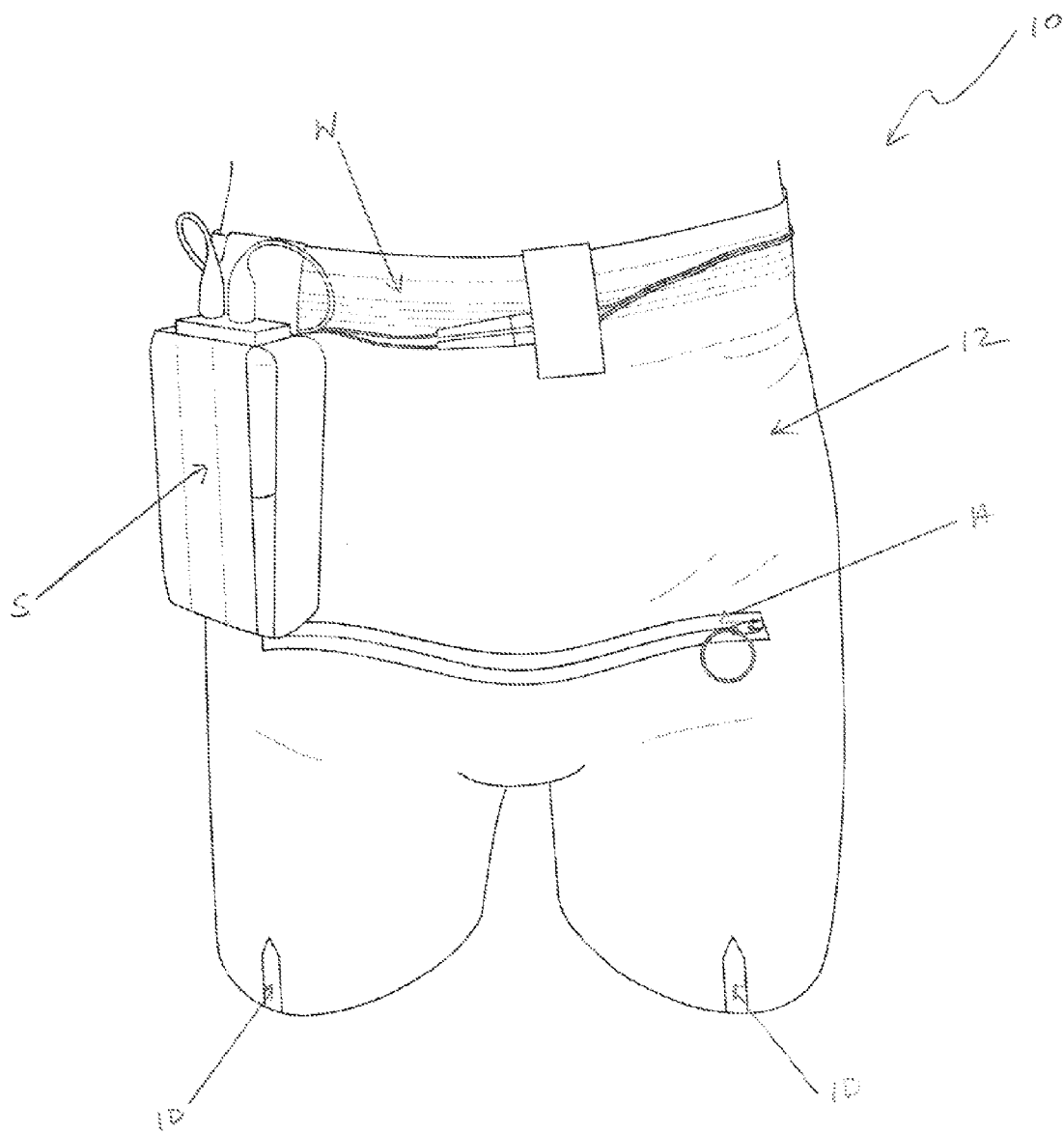
FIG. 1 shows a front view of an exemplary pant-like garment embodiment for electrically stimulating a loaded muscle(s)
Figure 2:
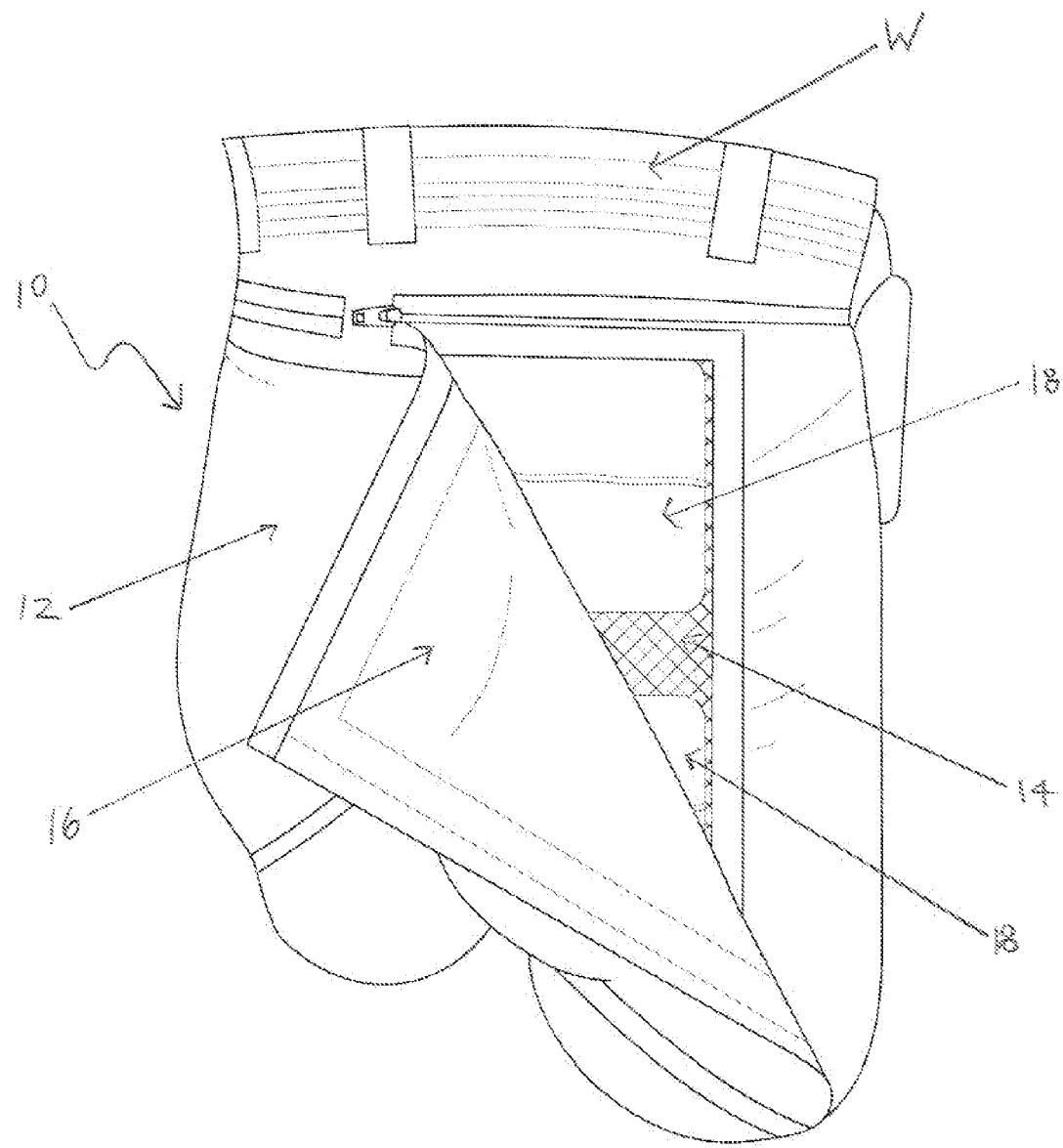
FIG. 2 shows a rear view of the exemplary pant-like garment embodiment for electrically stimulating a loaded muscle(s)

Having regard to FIGS. 1 and 2, the main body portion 12 may be fabricated from a stretchable (flexible), yet taut and form-fitting material. For example, the main body portion 12 may be fabricated from tight, non-wrinkling, elastomeric or cotton-based material (e.g. high tear strength cotton-spandex blend, cotton polyester), such as LYCRA®, COOLMAX®, SPANDEX® or the like. Preferably, the material may be thin, breathable and comfortable to wear under pants, skirts or dresses, or for extended periods of time. The main body portion 12 may be fabricated from material that provides a garment 10 that can be used (e.g. worn by an individual having compromised mobility) for extended periods of time (e.g. up to 24 hours/day) without casuing skin redness, irritation or breakdown. Further, garment 10 may be easily and accurately put on and taken off for washing, where desired.

Figure 3:
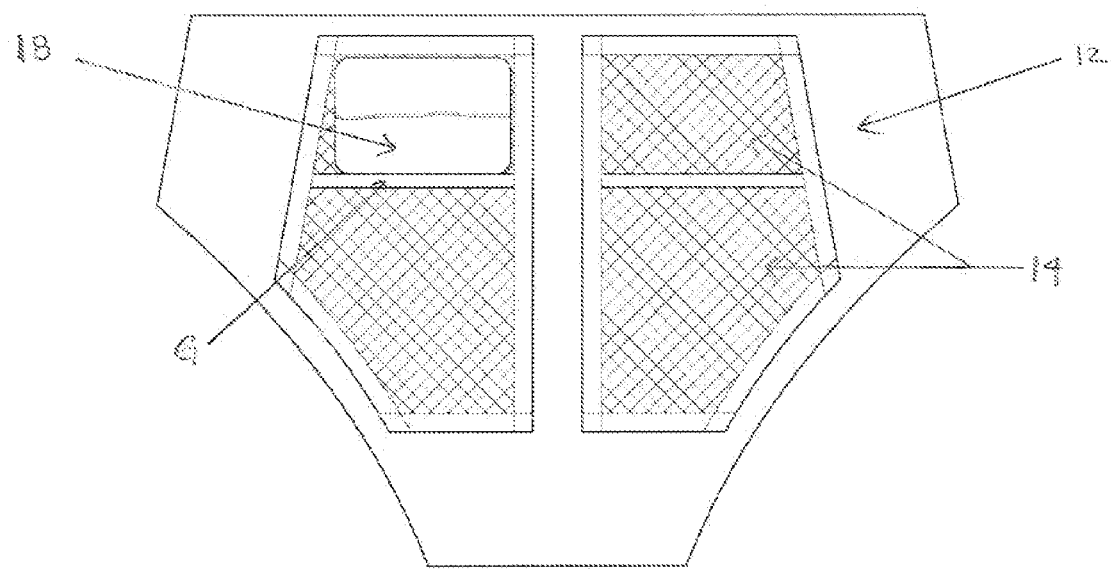
FIG. 3 shows a zoomed in rear view of the exemplary pant-like garment embodiment, wherein the back panel is removed.
Figure 4:
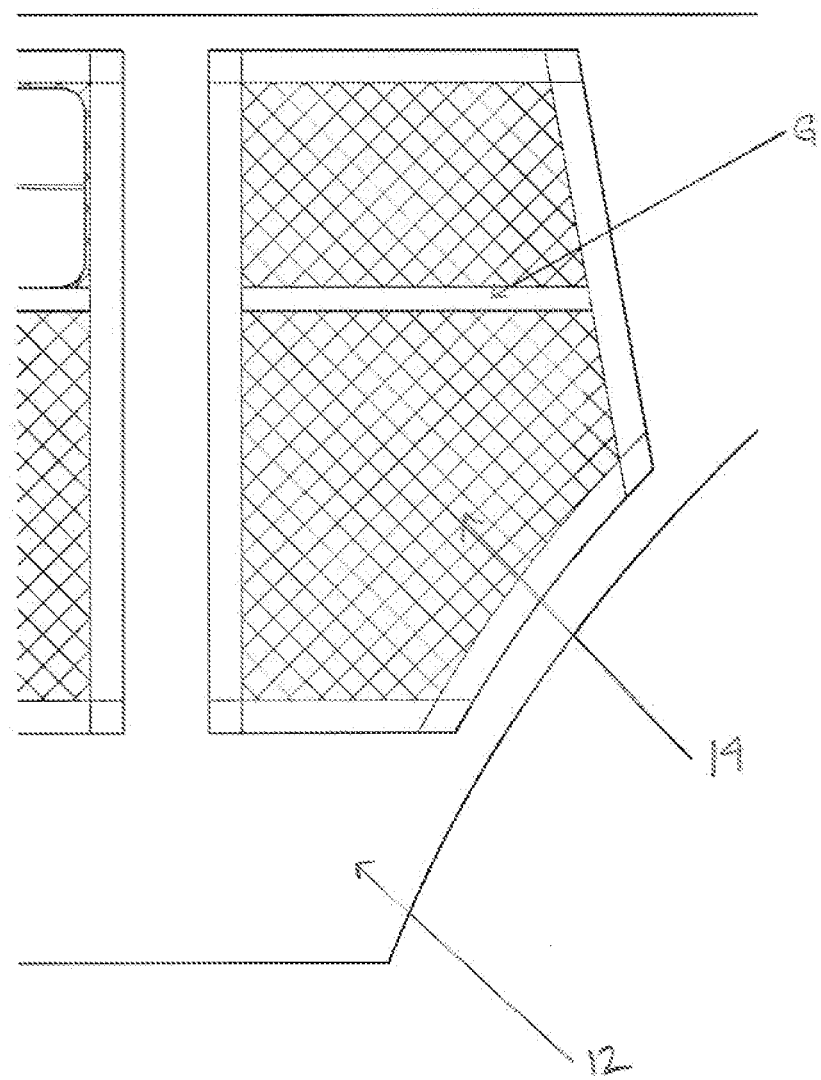
FIG. 4 is a further zoomed in view of the pant-like garment embodiment shown in FIG. 3.

Having regard to FIGS. 3 and 4, the at least one "opening" portion 14 may be fabricated from non-stretchy material having holes therein (i.e. permeable). For example, the at least one opening portion 14 may comprise thin, non-wrinkling micro mesh or netting (e.g. breathable polyester micromesh, Richard's Home, Portland, Oreg., USA). Garment 10 may be designed such that the at least one opening portion(s) 14 may be positioned at or near the wearer's loaded or compressed muscle—that is, the target muscle or muscle group being stimulated. The size and shape of opening portion(s) 14 may vary depending upon the size (e.g. small, medium, large) and shape (e.g. male, female) of the wearer and the location of their target muscles, provided that opening portion(s) be adequately sized to stimulate the wearer's target loaded muscle(s). For example, opening portion(s) 14 may range from approximately 3½ inches (top to bottom)×5 inches (across) to approximately 6 inches (top to bottom)×5½ inches (across). Garment 10 be fabricated to comprise a suitable ratio between stretchy main body portion 12 and non-stretchy opening portion(s) 14, such that garment 10 is stretchy enough to be put on and worn by the wearer without tearing, while being sufficiently form-fitting to enable electrical stimulation of the wearer's skin and muscle. Further, opening portion(s) 14 may be of sufficient size and shape to enable variations in electrode placement, thereby increasing likelihood of capturing the target motor point (e.g. tapered shape), and to minimize EMS-related discomfort and potential injury such as, for example, autonomic dysreflexia. Opening portion(s) 14 may optionally provide means for guiding appropriate electrode placement (G).

In one embodiment, garment 10 may be fabricated to minimize further mechanical pressure injury. For example (and having regard to FIG. 4), garment 10 may be fabricated using thin, iron-on seam tape (e.g. SewkeysE by Emma Seabrooke, Extremely Fine Fusible Knit Stay Tape), to join main body portion 14 and opening portion(s) 14, thereby minimizing seam thickness. Seam tape may adhere to main body 12 through the holes of mesh opening portion(s) 14. Where desired, the seam may be reinforced with one or more single stitches in order to strengthen the connection between the stretchy main body 12 and the non-stretchy opening portion(s) 14. In one embodiment, both main body portion 12 and opening portion(s) 14 comprise non-conductive material.

At least one electrode (and corresponding return) 18 may be positioned within garment 10 and operably linked to a stimulator (S) or any other small device for delivering an electrical stimulus. For example, electrodes 18 may comprise commercially-available, flexible, adhesive electrodes having sufficient size and shape to electrically stimulate a loaded muscle, and to effect contraction thereof (e.g. PALS® Platinum Neurostimulation Electrodes, Axelgaard Manufacturing Co., Ltd, Fallbrook, Calif., USA). It is desirable that electrodes 18 are selected and incorporated to rest as flush as possible with the body of the wearer.

In one embodiment, electrodes 18 may be removably secured in the at least one opening portion(s) 14 of garment 10. Electrodes 18 may be positioned on the external (non-skin) side of the at least one opening portion(s) 14, such that the at least one opening portion 14 is between the skin and electrode, thereby serving as a physical barrier minimizing adhesion (but not electrical conductivity) between electrodes 18 and the skin of the wearer. Such positioning of the electrodes 18 may retain sufficient electrical conductivity between electrodes 18 and the skin to effect stimulation of the wearer's muscle and skin (i.e. low impedance), while reducing injury caused by direct electrode-skin interfacing. Further, such electrode 18 positioning may minimize the requirement for conductivity enhancers such as, for example, liquid conductors, water or runny gels.

Figure 5:
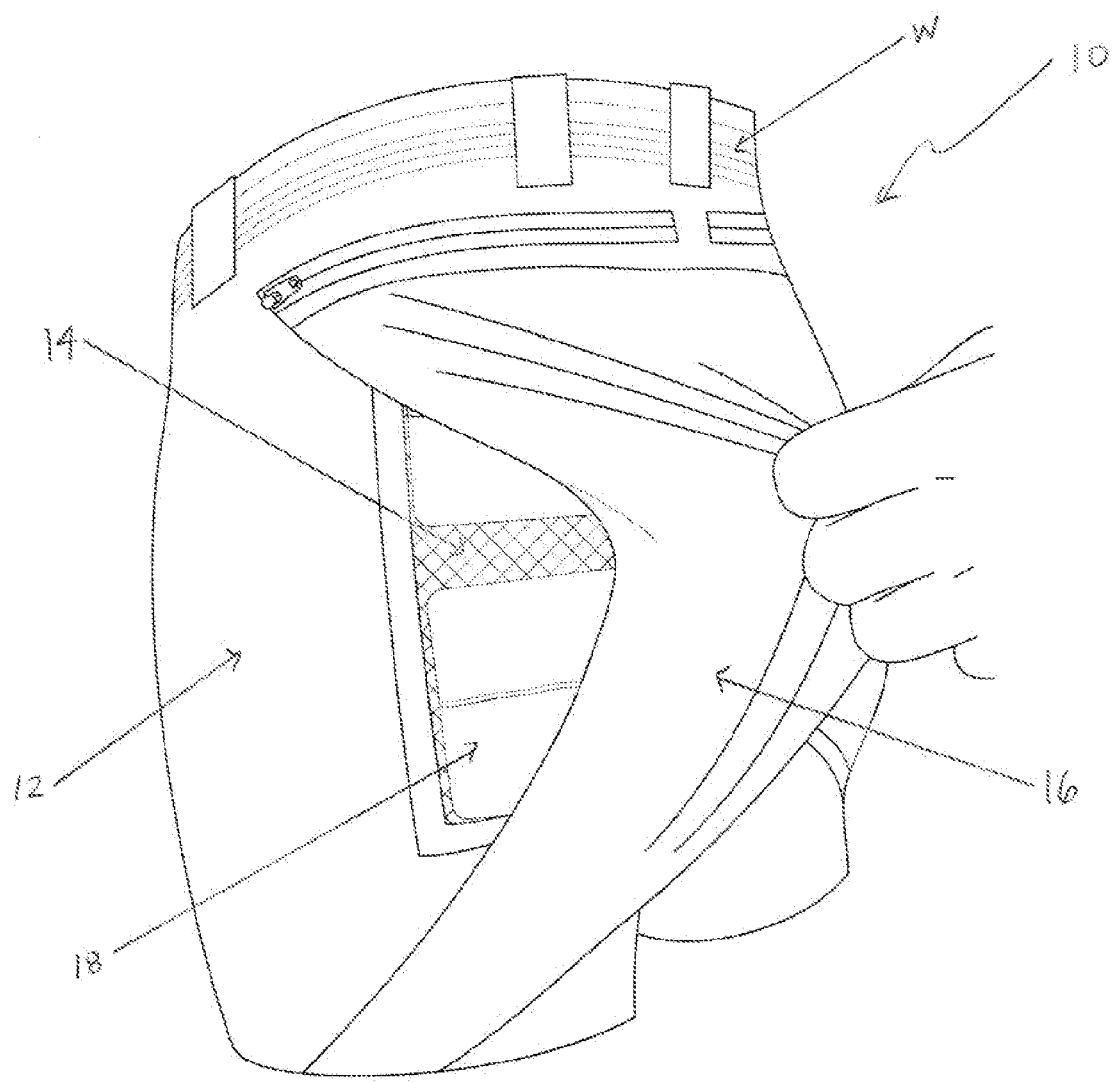
FIG. 5 shows a rear view of the exemplary pant-like garment embodiment having a loose-fitting back panel cover.

Having regard to FIG. 5, back panel portion 16 may be fabricated from friction-resistant, loose-fitting material capable of covering opening portion(s) 14 and electrodes 18. Back panel portion 16 may provide means for preventing inadvertent rolling, peeling or tugging (e.g. "catching" or "snagging") of electrodes 18 resulting from the wearer rubbing up against the external environment during regular daily movements (e.g. movement against a bed or wheelchair). Shifting or dislodging of the electrodes 18 can prevent effective delivery of EMS and cause injury from tugging and pulling on the skin (causing skin breakdown). Back panel portion 16 may further provide sufficient friction between the wearer and the external environment to prevent the wearer from slipping (e.g. slipping off the wheelchair seat).

In one embodiment, back panel 16 may be stretchy or non-stretchy material. Preferably, back panel 16 comprises stretchy material. Back panel 16 may generally correspond in size and shape to opening portion(s) 14. For example, where opening portion(s) 14 comprise a tapered shape, back panel 16 may also comprise a tapered shape. Preferably, back panel 16 may be opened in order to provide greater access to opening portion(s) 14.

Having regard to FIGS. 6 and 7, a second exemplary shirt-like garment 20 may similarly be a composite design having a main body portion 22 and opening portion(s) 24. Having regard to FIG. 7, main body portion 22 may be entirely or near-entirely configured of mesh material. Garment 20 may further comprise back panel portion (not shown) or a second shirt may be worn over top of garment 20.

The present garments 10, 20 may be utilized by a mobility-impaired individual simply by placing the main body portion 12, 22 on their body, connecting electrodes 18 to the programmable electrical stimulator (S), and running a pre-programmed electrical stimulation routine. The user of garments 10, 20 may removably position adhesive electrodes 18 within opening portion(s) 14, 24 before or after placing the garment on their body, whichever method is preferred and with or without the assistance of a caregiver. Where a caregiver assists the wearer, it is further provided that the modesty of the patient may be preserved by providing that the electrodes be positioned on the garment, rather than on the exposed (e.g. naked) skin of the patient. Electrode 18 should have a sufficiently long length to reach stimulator (S), without too much slack to prevent bundling of wires.

The electrical stimulator (S) may be automatically or manually programmed, such that garments 10, 20 may provide a means for applying EMS treatment to a person's loaded muscle and skin in an easily reproducible, repeatable and reliable manner, thereby allowing for consistent and continuous application of electrical stimulus on an hourly, daily or weekly basis. The present garments 10, 20 may be configured such that one or both sides of the person may be stimulated and modulated simultaneously or independently from one another.

Garments 10, 20 may be designed such they need not be removed from the person (and treatment need not be interrupted) during the daily care of the person. For example, having regard to FIG. 1, garment 10 may further comprise appropriately placed apertures (A) enabling catheterization to be performed without removal of garment 10. Apertures (A) may be located and designed to allow for the form-fitting shape of garment 10 to be retained and electrodes 18 to remain in position.

Garments 10, 20 may be designed for easy application and removal. For example, garment 10 may comprise a comfortable elastic waist band means (W) for maintaining the position of the garment 10 on the wearer.

Garments 10, 20 may be designed for consistent and repeatable positioning. For example, garment 10 may comprise means, such as identification marks (ID), for ensuring that garment 10 is accurately positioned on the wearer (e.g. not twisted), following day-to-day activities (such as toileting activities other than catheterization). Further, garments 10, 20 may be readily configured for males or females having different sizes and shapes.

Having regard to FIGS. 8 and 9, a third exemplary mattress pad cover or sheet-like embodiment 30 of the present apparatus, sheet 30 may be in the form of a cover for bed mattresses. Sheet 30 may comprise main body portion 32, forming opening portion(s) 34 therein. Opening portion(s) 34 may be positioned at or near the upper body (e.g. shoulders) and/or the lower body (e.g. pelvic region) of an individual lying on the mattress. In one embodiment, opening portion(s) may comprise one continuous, unitary mesh portion at or near the appropriate motor point (not shown). Main body portion 32 may be a mattress-fitting sheet fabricated from a stretchy, non-conductive material. Opening portion(s) 34 may be fabricated from a non-stretchy, porous (e.g. mesh) material. Main body portion 32 may be applied over a regular mattress protector and cover to effect delivery of electrical stimulation to the muscle and skin of a person lying on a bed. It is understood that opening portion(s) 34 may comprise at least one opening portion. It is understood that sheet 30 may further comprise a back panel portion (not shown) to prevent tugging or pulling on electrodes by the mattress of the bed. Arrays of electrodes (commercially-available, adhesive electrodes—not shown) may be applied to the inner (under) side of sheet 30 to effect activation or stimulation of the person's loaded muscles.

The election of electrodes (or pairs of electrodes) used for the delivery of the electrical stimulus may be manually selected based upon the position of the person on the mattress. In one embodiment, the choice and position of the electrodes may be facilitated by the use of an underlying pressure mattress or sensors embedded in the opening portion(s) between the electrodes capable of indicating the position of the patient in the bed and the location of loaded muscles, thereby identifying points of high pressure. In such a case, target regions may be identified and stimulated through appropriate electrodes at or near the target region.

In another embodiment, the choice and position of the electrodes may be performed automatically. For example, a microprocessor (not shown) may be used to identify regions of high pressure based upon the readings for an underlying pressure sensing mattress or embedded sensors. Electrodes within the region of the high pressure can be automatically chosen for stimulation. Activated electrodes can vary and be updated based upon changes in the position of the patient in the bed. As such, sheet 30 may include an array of flexible pressure sensors 36 positioned adjacent to the electrode array, rather than relying upon an underlying pressure mattress. This allows for a complete, all inclusive sensing and stimulating mesh.

The present sheet 30 may be configured such that one or both sides of the person may be stimulated and modulated simultaneously or independently from one another.

The present apparatus and method of use may further be utilized to prevent pressure ulcers in individuals suffering from incontinence. In one embodiment, the present apparatus and method may be a garment provided in the form of an incontinent product.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the description herein.

We claim:

1. A garment for preventing pressure ulcers in a loaded muscle(s), the garment comprising:
    a stretchy, form-fitting main body portion,
    at least one non-stretchy, opening portion comprising a layer of material forming holes therein or mesh material joined and positioned within the main body portion at or near the loaded muscles,
    at least one electrode, removably received and secured by the opening portion on an external side of the opening portion, and operably linked to a stimulator for delivering an electrical stimulus for stimulating the loaded muscles, to effect contraction thereof, and to redistribute pressure of the loaded muscles and increase oxygenation.

2. The garment of claim 1, wherein the at least one opening portion is positioned between the at least one electrode and the loaded muscle.

3. The garment of claim 1, wherein the at least one electrode stimulates the loaded muscle through the holes in the at least one opening portion(s).

4. The garment of claim 1, wherein the at least one electrode adheres to the at least one opening portion.

5. The garment of claim 1, wherein the garment minimizes adhesion of the at least one electrode with the loaded muscles, while retaining electrical conductivity with the loaded muscles.

6. The garment of claim 1, wherein the garment further comprises at one least one loose-fitting back panel portion for covering the at least one opening portion.

7. The garment of claim 6, wherein the back panel portion moves independently of the main body portion, the at least one opening portion or the at least one electrode.

8. The garment of claim 1, wherein the main body portion, the at least one opening portion or both comprise non-conductive material.

9. The garment of claim 1, wherein the main body portion is formed to cover a person's upper body, lower body or both.

10. An apparatus for preventing pressure ulcers in a loaded muscle(s) of an individual having compromised mobility, the apparatus comprising:
    a stretchy, form-fitting main body portion,
    at least one non-stretchy, opening portion comprising a layer of material forming holes therein or mesh material joined and positioned within the main body portion at or near the loaded muscle(s),
    at least one electrode, removably positioned within the opening portion on an external side of the opening portion, and operably linked to a stimulator for delivering an electrical stimulus for stimulating the loaded muscle(s), to effect contraction thereof, to redistribute pressure of the loaded muscle and increase oxygenation.

11. The apparatus of claim 10, wherein the at least one opening portion is positioned between the at least one electrode and the loaded muscle.

12. The apparatus of claim 10, wherein the at least one opening portion is formed from permeable material.

13. The apparatus of claim 10, wherein the at least one electrode stimulates the loaded muscle through the at least one opening portion.

14. The apparatus of claim 13, wherein the garment reduces adhesion of the at least one electrode with the loaded muscles.

15. The apparatus of claim 10, wherein the apparatus may be selected from the group comprising a garment covering a person's upper body, a garment covering a person's lower body, a garment covering a person's upper and lower body, a sheet or a mattress-pad cover.

16. The apparatus in claim 10, wherein the individual is incontinent and the apparatus is in the form of an incontinent product.

17. A method of stimulating loaded muscles in a person having compromised mobility, the method comprising:
    a. providing an apparatus capable of stimulating at least a portion of the loaded muscle, wherein the apparatus comprises:
        i. a stretchy, form-fitting main body portion,
        ii. at least one non-stretchy, opening portion comprising a layer of material forming holes therein or mesh material joined and positioned within the main body portion at or near the loaded muscle,
        iii. at least one electrode, removably received and secured by the opening portion on an external side of the opening portion, and operably linked to a stimulator for delivering an electrical stimulus for stimulating the loaded muscles,
    b. stimulating the loaded muscles, through the at least one opening portion, to effect contraction of the loaded muscles, wherein contraction redistributes pressure and increases oxygenation in the loaded muscle.

18. The method of claim 17, wherein the apparatus comprises a sheet or mattress-pad cover, or a garment covering the person's upper body, lower body or both.

* * * * *